United States Patent
Rehe

(10) Patent No.: US 9,888,835 B2
(45) Date of Patent: Feb. 13, 2018

(54) ENDOSCOPE AND ENDOSCOPY METHOD

(71) Applicant: Henke-Sass, Wolf GmbH, Tuttlingen (DE)

(72) Inventor: Oliver Rehe, Tuttlingen (DE)

(73) Assignee: Henke-Sass, Wolf GmbH, Tuttlingen (DE)

( * ) Notice: Subject to any disclaimer, the term of this patent is extended or adjusted under 35 U.S.C. 154(b) by 690 days.

(21) Appl. No.: 14/306,199

(22) Filed: Jun. 16, 2014

(65) Prior Publication Data

US 2014/0378769 A1    Dec. 25, 2014

(30) Foreign Application Priority Data

Jun. 25, 2013 (DE) .................. 10 2013 212 111

(51) Int. Cl.
| | |
|---|---|
| *A61B 1/00* | (2006.01) |
| *G02B 23/24* | (2006.01) |
| *G02B 23/26* | (2006.01) |
| *G02B 27/00* | (2006.01) |
| *G02B 27/10* | (2006.01) |
| *G02B 27/14* | (2006.01) |
| *A61B 1/002* | (2006.01) |
| *A61B 5/00* | (2006.01) |
| *G02B 15/173* | (2006.01) |
| *A61B 1/04* | (2006.01) |

(52) U.S. Cl.
CPC .......... *A61B 1/00163* (2013.01); *A61B 1/002* (2013.01); *A61B 1/00186* (2013.01); *A61B 5/0075* (2013.01); *G02B 23/2446* (2013.01); *G02B 23/2453* (2013.01); *G02B 23/26* (2013.01); *G02B 27/005* (2013.01); *G02B 27/1006* (2013.01); *A61B 1/042* (2013.01); *G02B 15/173* (2013.01); *G02B 27/141* (2013.01)

(58) Field of Classification Search
CPC . A61B 1/00163; A61B 1/00186; A61B 1/002; G02B 15/173; G02B 23/2446; G02B 23/26; G02B 27/005; G02B 27/141
See application file for complete search history.

(56) References Cited

U.S. PATENT DOCUMENTS

| | | |
|---|---|---|
| 2011/0249323 A1 | 10/2011 | Tesar et al. |
| 2012/0002956 A1 | 1/2012 | McDowall |

FOREIGN PATENT DOCUMENTS

| | | |
|---|---|---|
| DE | 102005032515 A1 | 1/2007 |

*Primary Examiner* — Timothy J Neal
*Assistant Examiner* — Aaron B Fairchild
(74) *Attorney, Agent, or Firm* — Skaar Ulbrich Macari, P.A.

(57) ABSTRACT

An endoscope is provided with a main part, an endoscope shaft and an imaging lens system. An imaging lens system includes a correction module, which comprises a splitter unit and a superimposition unit. Light is routed to the correction module via a first beam path, which is split into a first and a second partial beam path by the splitter unit. The splitter unit guides light from the visible spectrum into one of the two partial beam paths and light from the near infrared range into the other partial beam path. The superimposition unit superimposes the light from the two partial beam paths and guides it into a second beam path, coaxial with the first beam path. The optical path lengths of the two partial beam paths for the light from the visible spectrum and the light from the near infrared range are selected such that they are different.

13 Claims, 1 Drawing Sheet

ENDOSCOPE AND ENDOSCOPY METHOD

PRIORITY

This application claims priority to German Patent Application No. 102013212111.3, filed on Jun. 25, 2013, which is hereby incorporated herein by reference in its entirety.

FIELD

The present invention relates to an endoscope and an endoscopy method which are suitable for imaging both in the visible spectrum and in the near infrared range.

BACKGROUND

If imaging both in the visible spectrum and in the near infrared range is to be carried out, the difficulty often arises that known endoscopes (in particular their imaging lens systems) are not designed for this. This then leads to the focal plane for light from the visible spectrum not coinciding with the focal plane for light from the near infrared range. This distance between the two focal planes which is present in the axial direction is often called longitudinal chromatic aberration.

It is known from US 2011/0249323 A1 to join together two dove prisms on their longest sides and to provide a dichroic splitter layer therebetween in order to thus guide light from the visible spectrum substantially in one of the two dove prisms and light from the near infrared range substantially in the other of the two dove prisms and then to superimpose it again (FIG. 3 of US 2011/0249323 A1). The optical path lengths can be set such that they are different by the choice of the prism materials. A disadvantage here, however, is that on the one hand a lateral offset is present between the incident light ray in the prism arrangement and the exiting light ray from the prism arrangement. In addition, the compensation of the longitudinal chromatic aberration takes place purely via the different materials, as the geometric paths for light from the visible spectrum and light from the near infrared range are the same, with the result that the possibility for compensation of the longitudinal chromatic aberration is severely limited.

SUMMARY

An object of the invention includes providing an endoscope and an endoscopy method in which a good correction of the longitudinal chromatic aberration is possible.

According to certain embodiments, the object is achieved by an endoscope comprising a main part, an endoscope shaft connected to the main part and an imaging lens system, arranged inside the endoscope shaft and the main part, which images an object, located in front of the end of the endoscope shaft facing away from the main part, into a focal plane of the imaging lens system, wherein the imaging lens system has a correction module, arranged in the main part, through which light is guided to image the object and which comprises a splitter unit and a superimposition unit, wherein the light is routed to the correction module via a first beam path, which is split into a first and a second partial beam path by means of the splitter unit, wherein the splitter unit guides light from the visible spectrum into one of the two partial beam paths and light from the near infrared range into the other of the two partial beam paths, and the superimposition unit superimposes the light from the two partial beam paths and guides it into a second beam path, which runs coaxially with the first beam path, wherein the optical path lengths of the two partial beam paths for the light from the visible spectrum and the light from the near infrared range are selected different such that the longitudinal chromatic aberration in the area of the focal plane between the light from the visible spectrum and the light from the near infrared range is compensated for.

By the coaxial arrangement of the two beam paths, it is advantageously achieved that the lateral extension of the correction module can be minimized. Furthermore, the difference between the optical path lengths can be freely set independently of the lateral extension over the lengths of the two partial beam paths and of the materials used therein.

The compensation, or correction, of the longitudinal chromatic aberration can be partial or complete. In any case the longitudinal chromatic aberration is reduced.

In the case of the endoscope according to certain embodiments of the invention, the correction module is, in particular, free from imaging optical elements. It thus preferably has no curved, and thus optically effective, boundary surface. All boundary surfaces present are preferably formed flat.

The correction module can be preferably configured as an afocal correction module.

The correction module can be produced without major effort and thus also cost-effectively.

In particular embodiments, the first partial beam path can be coaxial with the two beam paths. It is thus possible that the lateral extension (thus transverse to the longitudinal direction of the two beam paths) of the correction module is as small as possible.

Furthermore, the second partial beam path can have a section which is parallel to both beam paths. This makes the production of the correction module easier, as such a section of the second partial beam path can be achieved by bendings of the beam path at right angles only.

In the case of the endoscope according to certain embodiment of the invention, the partial beam path in which the light from the near infrared range is guided can include a block which extends rectilinearly with a first refractive index, and the partial beam path in which the light from the visible spectrum is guided can have a medium (e.g. air) with a second refractive index, wherein the first refractive index for the light from the near infrared range is greater that the second refractive index for the light from the visible spectrum.

The medium can be comfigured e.g. gaseous and the block which extends rectilinearly can be configured e.g. as a solid (for example made from glass or plastic). Furthermore, it is possible that the medium is configured as a solid (e.g. glass or plastic).

The first partial beam path can be rectilinear and the second partial beam path can be U-shaped.

In the case of the endoscope according to certain embodiments of the invention, the splitter unit and the superimposition unit can in each case be configured as a splitter cube.

The second partial beam path can include two deflecting prisms. In certyain embodiments, each deflecting prism can be in mechanical contact with a splitter cube in each case.

The second partial beam path can include a rectilinear block between the two deflecting prisms. The rectilinear block can be in mechanical contact with the two deflecting prisms.

The first partial beam path can additionally or alternatively include a block which extends rectilinearly and which is arranged between the two splitter cubes. In particular, the block can be in mechanical contact with both splitter cubes.

The endoscope according to certain embodiments of the invention can be configured as a medical or technical endoscope. The endoscope can be hermetically sealed or autoclavable.

The endoscope shaft can be configured as a rigid endoscope shaft, as an endoscope shaft with a distal end which can be angled, or as a flexible endoscope shaft.

The endoscope according to certain embodiments of the invention can include a camera connector on the end of the main part which faces away from the endoscope shaft, to which camera connector a camera can be attached with which the object imaged by means of the imaging lens system can be recorded. The camera can be configured such that it can record both an image with light from the visible spectrum and an image with light from the near infrared range (simultaneously and/or sequentially in time).

In particular embodiments, a system of the endoscope according to the various embodiments of the invention and a camera connected thereto is provided.

By light from the visible spectrum is meant here in particular light with a wavelength from the range of from 380 to 750 nm and in particular 400 to 700 nm. By light from the near infrared range is meant here in particular light with a wavelength from the range of from 700 nm to 3 µm, 780 nm to 3 µm, 700 to 1500 nm and in particular 780 to 1500 nm. In any case the wavelength ranges for light from the visible spectrum and light from the near infrared range do not overlap.

The focal plane of the imaging lens system can lie in the main part or behind the main part and thus outside the main part.

The first beam path preferably ends at the splitter unit of the correction module in certain embodiments. The second beam path preferably begins at the superimposition unit of the correction module. The two partial beam paths preferably run in each case from the splitter unit to the superimposition unit.

The endoscope according to various embodiments of the invention can include further elements known to a person skilled in the art which are necessary for operation of the endoscope according to the invention.

The object is further achieved in certain embodiments by an endoscopy method for an endoscope with a main part, an endoscope shaft connected to the main part and an imaging lens system, arranged inside the endoscope shaft and the main part, which images an object, located in front of the end of the endoscope shaft facing away from the main part, into a focal plane of the imaging lens system, wherein the imaging lens system in the main part splits the light routed via a first beam path into a first and a second partial beam path, wherein light from the visible spectrum is guided into one of the two partial beam paths and light from the near infrared range is guided into the other of the two partial beam paths and, after passing through the two partial beam paths, are superimposed and guided into a second beam path which runs coaxially with the first beam path, wherein the optical path lengths of the two partial beam paths for the light from the visible spectrum and the light from the near infrared range are selected different such that the longitudinal chromatic aberration in the area of the focal plane between the light from the visible spectrum and the light from the near infrared range is compensated for.

The endoscopy method according to certain embodiments of the invention can be developed such that it has the method steps described in connection with the endoscope according to the invention (including developments thereof). In the same manner, the endoscope according to certain embodiments of the invention (including developments thereof) can be developed such that the endoscopy method according to the invention (including developments thereof) can be carried out therewith.

It is understood that the features mentioned above and those yet to be explained below can be used not only in the stated combinations, but also in other combinations or alone, without departing from the scope of the present invention.

BRIEF DESCRIPTION OF THE DRAWINGS

The invention is explained in further detail below by way of example with reference to the attached drawings which also disclose features essential to the invention. There are shown in.

DETAILED DESCRIPTION

The present invention can be explained with reference to the following example embodiments. However, these example embodiments are not intended to limit the present invention to any specific examples, embodiments, environments, applications or implementations described in these embodiments. Therefore, description of these embodiments is only for purpose of illustration rather than to limit the present invention.

Figure 1:
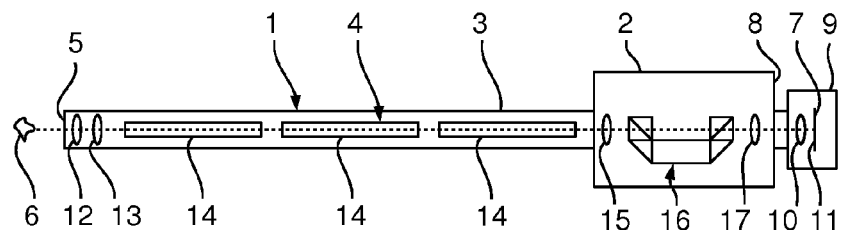
FIG. 1 is a schematic view of an embodiment of the endoscope according to the invention.

In the case of the embodiment shown in FIG. 1, the endoscope 1 includes a main part 2 and an endoscope shaft 3 connected to the main part 2. The endoscope 1 comprises an imaging lens system 4, which images an object 6, located in front of the distal end 5 of the endoscope shaft 3 facing away from the main part 2, into a focal plane 7 of the imaging lens system 4. As is represented schematically in FIG. 1, a camera 9 can be fixed (for example detachably) on the proximal end 8, facing away from the endoscope shaft 3, of the main part 2, which camera 9 has a camera lens system 10 and an acquisition sensor 11 arranged downstream of this. The imaging lens system 4 is preferably configured such that the focal plane 7 coincides with the position of the acquisition sensor 11, with the result that a sharp imaging of the object 6 can be carried out.

The camera lens system 10 can be configured as a separate coupler which can be fixed e.g. detachably on the proximal end 8 of the main part 2. A camera module with a corresponding acquisition sensor 11 can then in turn be fixed preferably detachably on the end of the coupler facing away from the main part 2. The coupler can for example provide a focussing function.

The endoscope 1 can be modified in additional embodiments such that the coupler is firmly connected to the main part 2. Furthermore, the coupler can also be integrated in the main part 2.

Referring to FIG. 1, the imaging lens system 4 comprises, in the direction from the distal end 5 towards the proximal end 8, a objective 12, a first optics module 13, three inversion systems 14 arranged one behind the other, a second optics module 15, a correction module 16, and an ocular 17. The object 6 is recorded by means of the objective 12 and coupled via the first optics module 13 into the first inversion system 14, which, in the same way as the two further inversion systems 14, conveys an image present on the input side in each case such that it is present imaged rotated by 180° at the output side. The three inversion systems 14, which are preferably configured as a rod lens system in each case, thus form a guidance system, with which the image of the recorded object 6 is guided to the main part 2, in which it is routed to the correction module 16 by means of the optics module 15 and then imaged via the ocular 17 such that it can be recorded by means of the camera 9. The imaging lens system 4 without the correction module 16 can be configured as is described for example in German patent application no. 10 2005 032 515 A1. The two optics modules 13 and 15 are optional and can optionally also be omitted.

As is further described in detail below, the correction module 16 serves to compensate for the longitudinal chromatic aberration in the area of the focal plane 7 between light from the visible spectrum and light from the near infrared range, as endoscopes are used more and more frequently to record an image in the near infrared range in addition to an image in the visible wavelength range. Thus, for example, fluorescent substances can be accumulated in cancerous tissue and be excited to fluorescence at 835 nm. However, since conventional imaging lens systems are corrected only for the visible range as a rule, the focal plane for light from the near infrared range does not lie in the focal plane 7 but behind it (to the right of it in FIG. 1). Designing the imaging lens system 4 such that it is also corrected for light from the near infrared range would lead to more optical elements being necessary, with the result that the production would become more laborious and more expensive. Moreover, as a rule there is very little space for the lens system precisely in the area of the endoscope shaft 3, with the result that this would disadvantageously potentially lead to a larger shaft diameter.

In the case of the endoscope 1 according to the invention, the correction module 16, which corrects this longitudinal chromatic aberration in the area of the focal plane 7, is therefore arranged in the main part.

Figure 2:
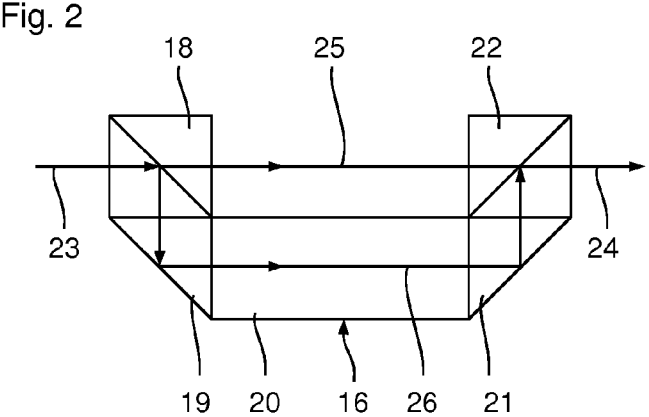
FIG. 2 is an enlarged view of the correction module of the imaging lens system.

For this, the correction module 16 has, as can be seen in the enlarged detail view in FIG. 2, a beam splitter 18, a first deflecting prism 19, a glass section 20, a second deflecting prism 21, and a beam combiner 22. The light coming from the second optics module 15 runs in a first beam path 23 to the beam splitter 18, which reflects light from the near infrared range towards the first deflecting prism 19 and transmits light from the visible spectrum. The light from the near infrared range is deflected by the first deflecting prism 19, passes through the glass section 20 and is then deflected by the second deflecting prism 21 towards the beam combiner 22. The beam combiner 22 reflects the light from the near infrared range and transmits the light from the visible spectrum which runs from the beam splitter 18 along a first partial beam path 25 to the beam combiner 22, with the result that the beam combiner 22 superimposes the light from the visible spectrum and the light from the near infrared range and guides the superimposed light along a second beam path 24 to the eyepiece 17.

The correction module 16 thus has different partial beam paths 25, 26, wherein the partial beam path for the light from the visible spectrum is denoted as first partial beam path 25 and the partial beam path for the light from the near infrared range is denoted as second partial beam path 26. The correction module 16 is thus now configured such that the optical path lengths in the two partial beam paths 25 and 26 are selected such that they are different. The difference in the optical path lengths is selected such that the longitudinal chromatic aberration in the area of the focal plane 7 is (preferably completely) compensated for. This is achieved in that the materials for the two partial beam paths 25 and 26 are selected such that they are different. Thus, for example, air with a refractive index $n_0$ of 1 for light from the visible spectrum is present in the first partial beam path. The beam splitter 18 and the beam combiner 22 have in each case a refractive index $n_1$ which is greater than the refractive index $n_0$. Thus, for example, the material N-BK10 can be used for the beam splitter 18 and the beam combiner 22, which has a refractive index of 1.49782 for the wavelength of 588 nm and of 1.49127 for a wavelength of 852 nm.

For the two deflecting prisms 19 and 21 and the glass section 20, a material with a refractive index $n_2$ is selected, which is greater for light from the near infrared range than the refractive index $n_0$ of the first partial beam path 25 for light from the visible spectrum. For example, S-LAH 79 with a refractive index of 1.97630 for a wavelength of 852 nm can be selected as material.

Via the choice of the length of the second partial beam path (thus the path for the light from the near infrared range in the first deflecting prism 19, in the glass section 20 and in the second deflecting prism 21) taking into account the corresponding refractive indices $n_0$, $n_1$ and $n_2$, the desired compensation of the longitudinal chromatic aberration can take place. The length of the glass section 20 thus can be substantially varied in order to achieve the desired necessary correction.

As the first and second beam paths 23, 24 are coaxial, the space required by the correction module 16 transverse to the longitudinal direction of the two beam paths 23 and 24 can be minimized. For light from the visible spectrum, the first beam path 23, the first partial beam path 25 and the second beam path 24 constitute a main beam path extending rectilinearly and only the light from the near infrared range is coupled out from this main beam path, guided over the second partial beam path 26 and then coupled back into the main beam path. The correction module 16 can thus easily be configured such that the desired compensation of the longitudinal chromatic aberration in the area of the focal plane 7 is achieved and the necessary spatial dimensions (in particular transverse to the longitudinal direction) of the beam paths 23, 24 can simultaneously be minimized. As the correction module 16 is arranged in the main part 2 of the endoscope, there is enough space for the correction module 16.

The embodiment with the beam splitter 18 and the beam combiner 22 as well as the two deflecting prisms 19 and 21 and the glass section 20 allows the individual elements to be cemented together. A substantially U-shaped glass structure is thus present which brings about the desired correction of longitudinal chromatic aberration.

Figure 3:
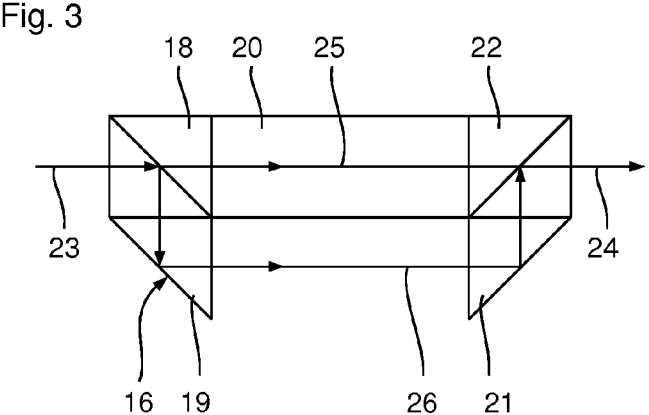
FIG. 3 is a modification of the correction module according to FIG. 2.

In FIG. 3 a modification of the correction module 16 is shown. In this case, the beam splitter 18 is configured such that it reflects light from the visible spectrum and transmits light from the near infrared range. Furthermore, the beam combiner 22 is configured such that it transmits light from the near infrared range and reflects light from the visible spectrum.

Here too, the advantage is achieved that the two beam paths 23 and 24 are arranged coaxially. In turn, a U-shaped glass structure is also present.

Of course, the partial beam path for the light from the visible spectrum does not have to run through air. A suitable glass material can also be selected. It is essential that the refractive index of this glass material for light from the visible spectrum is less than the refractive index of the glass section 20 for light from the near infrared range.

The correction module 16 is configured as an afocal correction module 16 and does not have a boundary surface which is configured curved (in particular no lens).

Of course, the elements of the correction module 16 need not be formed from glass. Any other substance is also possible. For example, plastic can be used.

The above disclosure is related to the detailed technical contents and inventive features thereof. People skilled in this field may proceed with a variety of modifications and replacements based on the disclosures and suggestions of the invention as described without departing from the characteristics thereof. Nevertheless, although such modifications and replacements are not fully disclosed in the above descriptions, they have substantially been covered in the following claims as appended.

The invention claimed is:

1. An endoscope, comprising:
   a main part;
   an endoscope shaft connected to the main part; and
   an imaging lens system, disposed inside the endoscope shaft and the main part, which images an object, located in front of the end of the endoscope shaft facing away from the main part, into a focal plane of the imaging lens system,
   wherein the imaging lens system includes a correction module, disposed in the main part, through which light is guided to image the object and which comprises a splitter unit and a superimposition unit,
   wherein the light is routed to the correction module via a first beam path, which is split into a first partial beam path and a second partial beam path by the splitter unit,
   wherein the splitter unit is configured to guide light from the visible spectrum into the first partial beam path and light from the near infrared range into the second partial beam path,
   wherein the superimposition unit is configured to superimpose the light from the first and second partial beam paths and guides the light into a second beam path, which is coaxial with the first beam path,
   wherein the optical path lengths of the two partial beam paths for the light from the visible spectrum and the light from the near infrared range are different to compensate for a longitudinal chromatic aberration in the area of the focal plane between the light from the visible spectrum and the light from the near infrared range, and
   wherein the main part comprises a camera connector on the end of the main part which faces away from the endoscope shaft
   wherein the correction module is configured as an afocal correction module.

2. The endoscope according to claim 1, wherein the correction module is free from imaging optical elements.

3. The endoscope according to claim 1, wherein the first partial beam path is coaxial with both beam paths.

4. The endoscope according to claim 1, wherein the second partial beam path includes a section that is parallel to the two beam paths.

5. The endoscope according to claim 1, wherein the partial beam path in which the light from the near infrared range is guided includes a block which extends rectilinearly with a first refractive index, and the partial beam path in which the light from the visible spectrum is guided includes a medium with a second refractive index, wherein the first refractive index for the light from the near infrared range is greater that the second refractive index for the light from the visible spectrum.

6. The endoscope according to claim 1, wherein the first partial beam path is rectilinear and the second partial beam path is U-shaped.

7. The endoscope according to claim 1, wherein each of the splitter unit and the superimposition unit are configured as a splitter cube.

8. The endoscope according to claim 7, wherein the first partial beam path includes a block, which is arranged between the two splitter cubes and which extends rectilinearly, and which is in mechanical contact with the two splitter cubes.

9. The endoscope according to claim 1, wherein the second partial beam path includes two deflecting prisms.

10. The endoscope according to claim 9, wherein the second partial beam path includes a block, which extends rectilinearly, which is arranged between the two deflecting prisms and is in mechanical contact with these.

11. The endoscope according to claim 1, wherein each of the splitter unit and the superimposition unit are configured as a splitter cube, and wherein the second partial beam path includes two deflecting prisms, each deflecting prism in mechanical contact with a respective one of the splitter cubes.

12. The endoscope according to claim 11, wherein the second partial beam path includes a block, which extends rectilinearly, which is arranged between the two deflecting prisms and is in mechanical contact with these.

13. An endoscopy method for an endoscope, comprising:
   providing a main part, an endoscope shaft connected to the main part and an imaging lens system, disposed inside the endoscope shaft and the main part, wherein the main part comprises a camera connector on the end of the main part which faces away from the endoscope shaft;
   imaging an object located in front of the end of the endoscope shaft facing away from the main part, into a focal plane of the imaging lens system;
   splitting the light routed via a first beam path into a first and a second partial beam path;
   guiding a visible spectrum of the light into the first of the first and second partial beam paths;
   guiding a near infrared range of the light into the second of the first and second partial beam paths;
   after passing the light through the first and second partial beam paths, superimposing and guided the light into a second beam path, which is coaxial with the first beam path,
   selecting different the optical path lengths of the first and second partial beam paths for the light from the visible spectrum and the light from the near infrared range to compensate for a longitudinal chromatic aberration in the area of the focal plane between the light from the visible spectrum and the light from the near infrared range wherein splitting the light and passing the light through the partial beam paths to the second beam path is afocal.

* * * * *